US011085806B2

(12) United States Patent
Rivera et al.

(10) Patent No.: US 11,085,806 B2
(45) Date of Patent: Aug. 10, 2021

(54) APPARATUS AND METHOD FOR LIQUID LEVEL MEASUREMENT AND CONTENT PURITY MEASUREMENT IN A SOUNDING TUBE

(71) Applicant: Vega Americas, Inc., Cincinnati, OH (US)

(72) Inventors: Esther Milagros Díaz Rivera, Mason, OH (US); Greggory James Garrett, Fayetteville, OH (US); Michael Ray Conley, Cincinnati, OH (US); Neil T. Wilkie, Saint Cloud, FL (US)

(73) Assignee: Vega Americas, Inc., Cincinnati, OH (US)

( * ) Notice: Subject to any disclaimer, the term of this patent is extended or adjusted under 35 U.S.C. 154(b) by 621 days.

(21) Appl. No.: 15/428,759

(22) Filed: Feb. 9, 2017

(65) Prior Publication Data

US 2017/0227392 A1 Aug. 10, 2017

Related U.S. Application Data

(60) Provisional application No. 62/293,324, filed on Feb. 9, 2016.

(51) Int. Cl.
*G01F 23/22* (2006.01)
*G01N 33/00* (2006.01)
*G01F 23/00* (2006.01)
*G01F 23/284* (2006.01)
*G01F 23/296* (2006.01)
*G01F 23/04* (2006.01)

(52) U.S. Cl.
CPC .......... *G01F 23/22* (2013.01); *G01F 23/0023* (2013.01); *G01F 23/04* (2013.01);
(Continued)

(58) Field of Classification Search
CPC ...... G01F 23/0023; G01F 23/04; G01F 23/22; G01F 23/284; G01F 23/296; G01F 23/00;
(Continued)

(56) References Cited

U.S. PATENT DOCUMENTS

| 6,292,131 B1 * | 9/2001 | Wilke | G01F 23/284 |
| | | | 342/124 |
| 6,337,655 B1 * | 1/2002 | Wilkie | G01F 23/284 |
| | | | 342/124 |

(Continued)

FOREIGN PATENT DOCUMENTS

WO 2004/022456 A2 3/2004

*Primary Examiner* — Nimeshkumar D Patel
*Assistant Examiner* — Gedeon M Kidanu
(74) *Attorney, Agent, or Firm* — Wood Herron & Evans LLP

(57) ABSTRACT

A level sensing apparatus (110) for attachment to a sounding tube to measure levels of content in a tank. The level sensing apparatus includes a housing (16) for enclosing components of the level sensing apparatus (20). These components include a transmitter and an antenna (18) operatively connected to the transmitter for directing electrical or mechanical waves in a direction away from the transmitter. The antenna is adapted to also receive electrical and mechanical waves. The apparatus further includes a sounding tube adaptor (32) sized for attachment to a sounding tube, and a connector assembly operatively attaching the housing to the sounding tube adaptor. The connector assembly enabling the housing to rotate relative to the sounding tube adaptor about a horizontal axis to expose an open end of the sounding tube. In use, the level sensing apparatus allows for pulse radar measurement of liquid levels in the tank. The housing may be rotated relative to the sounding tube to also allow for manual level measurements or sampling of the tank contents.

20 Claims, 15 Drawing Sheets

(52) U.S. Cl.
CPC .......... *G01F 23/284* (2013.01); *G01F 23/296* (2013.01); *G01N 33/00* (2013.01)

(58) Field of Classification Search
CPC ................ G01F 23/003; G01F 23/2928; G01F 23/2962; G01F 23/2968; G01F 25/0061; G01N 33/00; Y10S 367/908
See application file for complete search history.

(56) References Cited

U.S. PATENT DOCUMENTS

| | | | | |
|---|---|---|---|---|
| 6,538,598 B1* | 3/2003 | Wilkie | .................. | G01F 23/284 342/124 |
| 7,134,315 B1* | 11/2006 | Stigler | .................. | G01F 23/284 73/290 V |
| 8,009,085 B2* | 8/2011 | Kuhlow | .............. | G01F 25/0061 324/600 |
| 8,069,722 B1* | 12/2011 | Jannotta | ................ | G01F 23/00 73/290 V |
| 9,658,096 B2* | 5/2017 | Kleman | .............. | G01F 25/0061 |
| 2006/0055591 A1* | 3/2006 | Eriksson | ................ | G01S 7/034 342/124 |
| 2006/0201245 A1* | 9/2006 | Huber | ................ | G01F 23/2962 73/290 R |
| 2008/0079628 A1* | 4/2008 | Wilkie | .................. | G01F 23/284 342/124 |
| 2015/0377681 A1* | 12/2015 | Kleman | .............. | G01F 25/0061 73/290 V |

* cited by examiner

APPARATUS AND METHOD FOR LIQUID LEVEL MEASUREMENT AND CONTENT PURITY MEASUREMENT IN A SOUNDING TUBE

FIELD OF THE INVENTION

The present invention relates to pulse radar measurement and, more particularly, to a level sensing apparatus and method using pulse radar waves to measure the level of liquid in a storage tank while also allowing for manual measurement of the liquid.

BACKGROUND OF THE INVENTION

In many environments, various materials are stored and/or processed in tanks prior to or during their disposition. These materials include foods, beverages, pharmaceuticals and fuels. One particular and commonly-known use of such tanks involves the storage of fuel for various modes of transportation. These fuel tanks can range from a gas tank on a car to voluminous fuel tanks such as those located on Naval ships. In particular, aircraft carriers house multiple fuel tanks. These tanks are used to store jet fuel for the aircraft carried on the ship.

With storage tanks on Naval vessels, the ability to reliably determine the amount and purity of the contents of the tanks at any given time can be critical. Military readiness is often dependent on an adequate fuel supply. Additionally, accurate measurement of fuel usage directly translates into cost effectiveness in procuring a fuel supply for ships. As such, there are many benefits to accurately and reliably gauging the level of fuel in these tanks and, therefore, the Navy conducts regular measuring to determine fuel levels in storage tanks. In addition, the operation of high-performance jets is dependent on a low level of impurities in the fuel. Contaminates in the fuel can cause damage to jet components and can degrade performance in a manner that is hazardous to the occupants. Thus, in addition to measuring fuel levels, the Navy conducts regular checks on the purity of the fuel in the tanks.

The purity of fuel stored on Naval ships is determined by a method commonly-referred to as "thief sampling". In this process an elongate hollow tube, or "thief sampler", is dropped into the contents of a tank. Fuel from the tank fills the hollow recess of the thief sampler. The thief sampler is then retracted and the purity of the collected sample is measured by methods well-known in the art.

Methods for the determination of liquid levels include visual examination or the use of various apparatus that gauge the level of the fuel. In the particular situation of jet fuel on Naval ships, visual examination is obstructed by the location of the tanks within the bowels of the ship and by the voluminous size of the tanks. Because of the problems with visual examination, the Navy has traditionally performed manual fuel level measurements through a sounding tube using a plumb line with an attached plumb bob. The sounding tube is commonly a one-and-one-half inch diameter pipe located as part of the infrastructure of the ship. The sounding tube extends within the fuel tank and is open to the tank contents, to equalize the liquid level in the sounding tube with the liquid level in the tank. The sounding tube is not necessarily a linear pipe, but may include bends, in order to extend around other infrastructure of the ship. To measure fuel levels, the top of the sounding tube is opened and the plumb bob is dropped through the interior of the sounding tube to the bottom of the tube. The plumb bob is then retracted from the bottom of the sounding tube using the plumb line, and the liquid level measured by observing the moisture level created by the fuel on the plumb line. The Navy continues to use this plumb line and sounding tube measurement as a back-up manual method on ships.

Certain problems arise, however, from the plumb line method of liquid level measurement. First, jet fuel is clear and evaporates very rapidly, thereby enhancing the difficulty of visually assessing the plumb line to accurately determine the associated moisture level. Second, the plumb bob may break off the plumb line during use. Due to the difficulty involved, as a practical matter detached plumb bobs are not retrieved from sounding tubes. As a result, subsequent plumb bobs used for measurement may be impeded from falling to the bottom of the sounding tube, resulting in reduced measurement range.

Due to the problems with visual and plumb line liquid level measurement methods, non-contact level sensing gauges have been developed and adapted to be operatively connected to a sounding tube for quickly and reliably determining fuel levels in storage tanks. Several types of non-contact level sensing gauges have been developed including gauges that use radar transmitters or ultrasonic waves. A high degree of accuracy has been achieved by the use of level sensing gauges which monitor content levels by transmitting microwave pulses from an antenna toward the surface of the tank contents. These pulses are reflected from the contents back to the antenna. Other radar gauges use a continuous wave rather than microwave pulses. Radar signals are unaffected by noise, by extreme air turbulence, or by fluctuations in dielectric constant above a nominal minimum value, density, or conductivity. Even liquids having highly agitated surfaces or gas bubbles are usually reliably measured with radar gauges. Gas layering, such as that produced by solvents or gases, has virtually no adverse effect. Radar sensors are suitable for liquids, solids, powders, granules, dust, corrosive steam and vapors, regardless of the media characteristics, environment, low and high pressures, or temperatures. As such, radar sensors are well-suited for sensing fuel levels in the tanks of Naval ships.

While non-contact radar level sensing gauges have many advantages, problems can arise with these gauges when attempting the back-up manual sounding method of level measurement and fuel purity checks, as practiced by the Navy. Removal of the level sensing gauge from the sounding tube in order to use the plumb line is unwieldy and time consuming, and requires placing the highly sensitive gauge on the deck of the ship. In this location, the gauge is vulnerable to damage. Additionally, after a sample has been taken, the level sensing gauge must be reattached to the sounding tube, which can be time-consuming and require a recalibration of the gauge.

Level sensing apparatus have been developed that do not require complete removal of the radar level sensing gauge from the sounding tube in order to perform manual liquid level and purity measurements. In one example, the level sensing apparatus includes a latch door which seals off an orifice through which a plumb bob may be inserted. This level sensing apparatus and method of measuring is described in commonly-assigned U.S. Pat. Nos. 6,538,598 and 6,337,655. While these apparatus and methods have proven adequate for measuring the level of contents in storage tanks using both non-contact radar and manual, plumb line methods, the location of the latch door in the apparatus does not allow for samples of the tank contents to be collected in order to measure the purity of the fuel. In particular, the position of the latch door in the sidewall of the sounding tube adaptor is not suitable for insertion of a thief sampler.

To address this problem, a non-contact level sensing gauge has been developed which includes apparatus for lifting the level sensing gauge in a vertical direction away from the sounding tube opening, and then swiveling the gauge about a vertical shaft to move the housing out of alignment with the sounding tube. Lifting and swiveling the level sensing gauge enables the gauge to remain attached to the sounding tube adaptor, while allowing access to the open end of the sounding tube to conduct manual measurements including obtaining fuel samples. This level sensing gauge is described in commonly-assigned, U.S. Pat. No. 6,292,131, the contents of which are incorporated herein by reference. While this level sensing gauge eliminates the need to remove the gauge from the sounding tube to perform manual measurements, and also allows for the use of a thief sampler to collect fuel samples, the need to lift the apparatus prior to swiveling is awkward and requires a minimum of overhead room. Additionally, the lifting and swiveling movements can be unwieldy in the tight space available on a Naval ship. Additionally, during the lifting and swiveling motions the antenna in the gauge can lose alignment with the sounding tube, necessitating a recalibration.

Accordingly, a simplified, streamlined non-contact level sensing gauge is described herein which provides full access to an open end of the sounding tube, while also eliminating the problems associated with the prior non-contact level sensing apparatus and methods.

SUMMARY OF THE INVENTION

The level sensing apparatus and liquid level and content purity measurement methods described herein improve upon the aforementioned apparatus and methods by providing apparatus for rotating the level sensing gauge away from the sounding tube. As will be described herein, the improved level sensing apparatus can be rotated away from the sounding tube to fully expose the open end of the tube, and thereby allow access to the sounding tube for insertion of a thief sampler, plumb line and bob, or other manually insertable measuring device. Additionally, in the improved level sensing apparatus the connecting assembly between the level sensing gauge and sounding tube adaptor is separable to allow for removal and replacement of the level sensing gauge without the need to remove the sounding tube adaptor from the sounding tube. Further, the improved level sensing apparatus and methods provide for quick, efficient alignment between the antenna and sounding tube to optimally polarize the gauge following rotation of the gauge housing.

In a first aspect, a level sensing apparatus is provided for attachment to a sounding tube to measure content levels in a tank. The level sensing apparatus includes a housing for enclosing components of the level sensing apparatus. These components include a transmitter and an antenna operatively connected to the transmitter for directing electrical or mechanical waves in a direction away from the transmitter. The antenna being adapted to also receive electrical and mechanical waves. The apparatus further includes a sounding tube adaptor sized for attachment to a sounding tube, and a connector assembly operatively attaching the housing to the sounding tube adaptor. The connector assembly enabling the housing to rotate relative to the sounding tube adaptor about a horizontal axis to expose an open end of the sounding tube.

In a second aspect, a method is provided for measuring a level of, and determining a purity of, contents in a tank. The method includes providing a level sensing apparatus attached to a sounding tube, the level sensing apparatus having a housing and a transmitter disposed within and attached to the housing. An antenna is further provided and disposed within the housing. The antenna is operatively connected to the transmitter for directing electrical or mechanical waves in a direction away from the transmitter and receiving electrical or mechanical waves reflected from a contents surface in the direction of the antenna. The method further includes providing a sounding tube adaptor for attachment to a sounding tube. A connector assembly is also provided for operatively attaching the housing to the sounding tube adaptor; the connector assembly being adapted to allow the housing to rotate relative to the sounding tube adaptor about a horizontal axis. The method further includes directing the electrical or mechanical waves to a contents surface in the sounding tube by the use of the level sensing apparatus, receiving the electrical or mechanical waves from the contents surface in the sounding tube by the use of the level sensing apparatus, and obtaining a corresponding measurement of a level of the contents in the sounding tube from the level sensing apparatus. Further, the method includes rotating the housing away from the sounding tube adaptor to expose an open end of the sounding tube, collecting a sample of contents in the tank, and determining the purity of the sample. In addition, the method can include rotating the housing away from the sounding tube adaptor to expose an open end of the sounding tube, inserting a plumb bob into the open end of the sounding tube, allowing the plumb bob to reach the bottom of the sounding tube, retracting the plumb bob from the tube, reading a level mark on the plumb line, rotating the housing over the top of the sounding tube adaptor, and aligning the antenna with the sounding tube.

BRIEF DESCRIPTION OF THE DRAWINGS

The above advantages and features of the invention and embodiments thereof will be further apparent from the following drawings and detailed description, in which.

DETAILED DESCRIPTION

Figure 1:
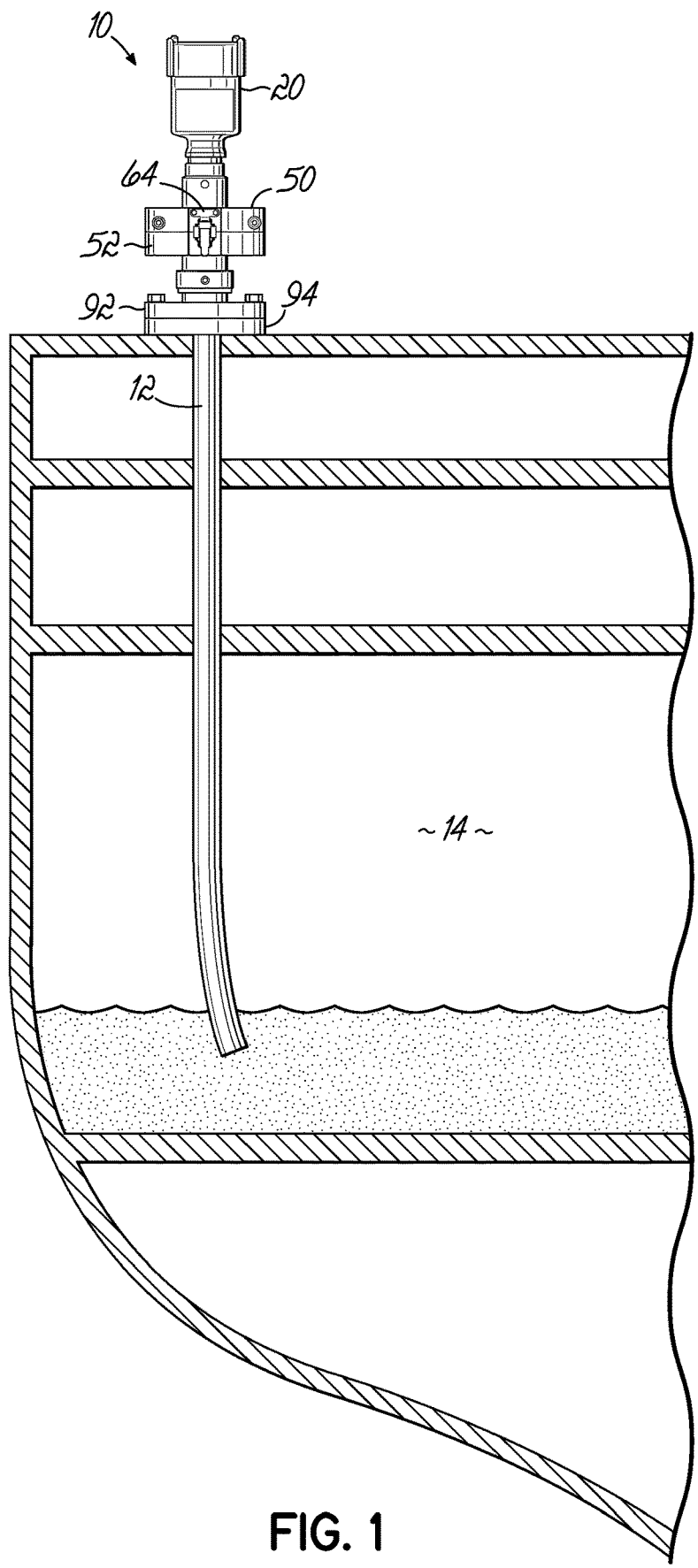
FIG. 1 is a diagrammatic view of a first exemplary embodiment of a level sensing apparatus attached to a sounding tube.

Referring now to the drawing figures, wherein like numerals indicate like elements through the views, FIG. 1 illustrates an exemplary embodiment of an improved, non-contact level sensing apparatus 10. Level sensing apparatus 10 is shown attached to a sounding tube 12 in order to measure levels of the contents of a storage tank 14. As shown in more detail in FIGS. 2 and 3, level sensing apparatus 10 includes a housing 16. Housing 16 comprises a transmitter cover 20, an adaptor 22 and an antenna shield 28, which together form a chamber for enclosing the operative components of the level sensing apparatus. These components include a transmitter 24, disposed within the transmitter cover 20, and an antenna assembly 26 having an antenna 18 operatively connected to the transmitter for directing electrical or mechanical waves in a direction away from the transmitter. The transmitter 24 may be, for example, a microwave transmitter, such as the VEGAPULS 66, which is commercially available from VEGA Americas, Inc., Cincinnati, Ohio. Antenna assembly 26 is further adapted to receive electrical or mechanical waves.

In the illustrated embodiment, the housing 16 includes a display 30 from which an operator may read the measurements of liquid levels in the tank 14. The transmitter 24 is mounted within the cover 20 in electrical communication with the antenna 18. The transmitter 24 generates electrical or mechanical waves used for measurement, and the antenna assembly 26 directs these waves in a direction away from the transmitter. These waves may be of various types including radar or ultrasonic waves. In at least one embodiment, microwave radar pulses are generated and transmitted by the apparatus 10. Other embodiments may use a continuous wave as opposed to radar pulses. Following transmittal, the waves are reflected off a surface to be measured and subsequently returned to the level sensing apparatus 10. The antenna assembly 26 is adapted to receive these reflected electrical or mechanical waves. In the illustrated embodiment, the distal end of the antenna assembly 26 protrudes below the open base of the antenna shield 28. In alternative embodiments, the distal end of the antenna assembly 26 may be entirely disposed within the cover 20, adaptor 22 and antenna shield 28.

Figure 2:
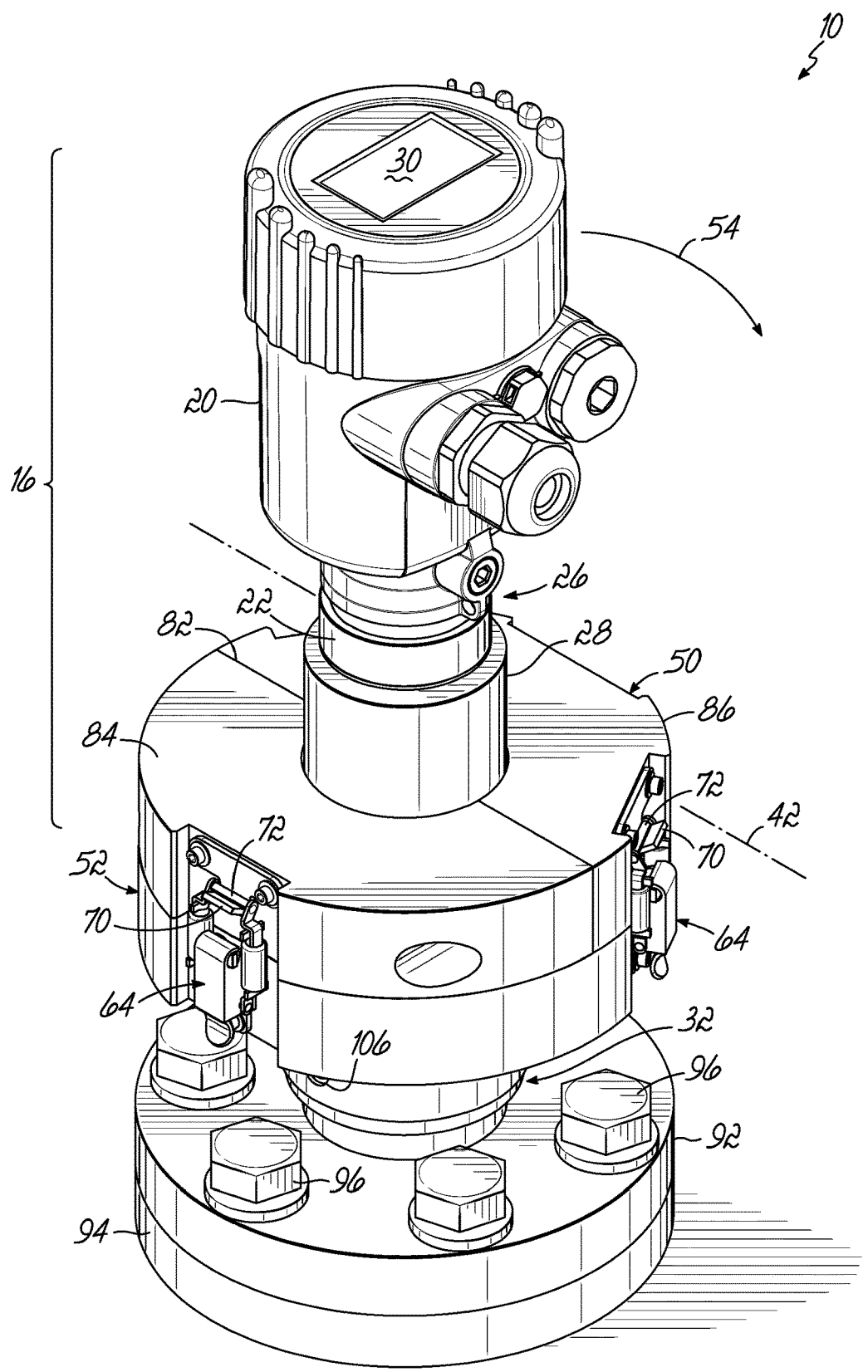
FIG. 2 is a perspective view of the exemplary level sensing apparatus of FIG. 1, depicting the apparatus in a closed, locked position.
Figure 3:
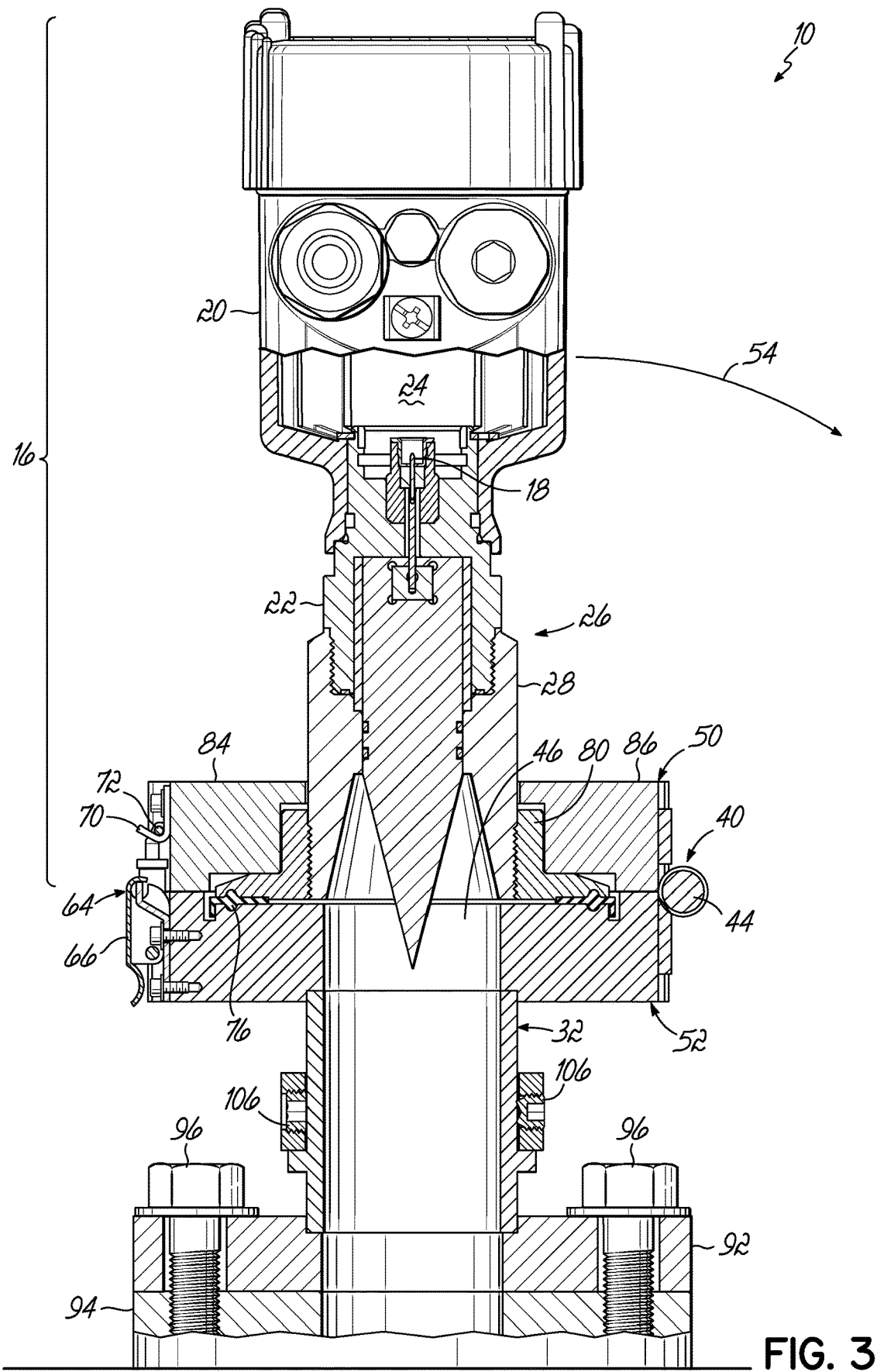
FIG. 3 is a plan view, partially in section, of the level sensing apparatus.
Figure 4:
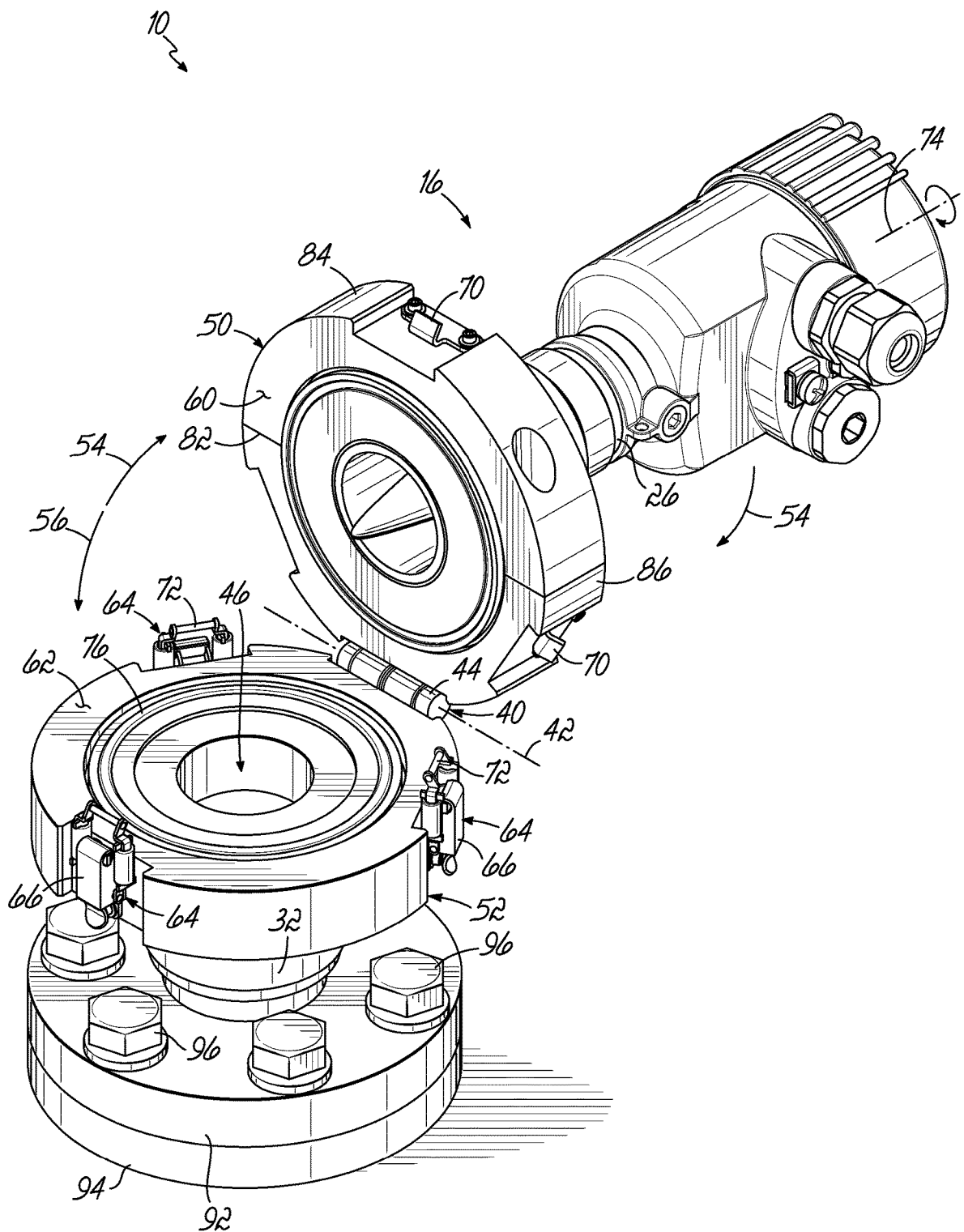
FIG. 4 is a perspective view depicting the level sensing apparatus in an open, unlocked position.

As shown in FIG. 3, the level sensing apparatus 10 also includes a sounding tube adaptor 32 configured for attachment to a sounding tube 12. Housing 16 is operatively connected to the sounding tube adaptor 32 by a connector assembly 40. The connector assembly 40 is adapted to allow the housing 16 to rotate relative to the sounding tube adaptor 32 about a horizontal axis 42, as shown in FIGS. 2 and 4. The connector assembly 40 includes a flexible joint 44 to enable the housing 16 to rotate relative to the sounding tube adaptor 32. Rotating housing 16 away from the sounding tube adaptor 32 exposes an opening 46 into the sounding tube 12, to allow for measurement of the purity of the tank contents, or to conduct a manual sounding of the tank 14.

Figure 5:
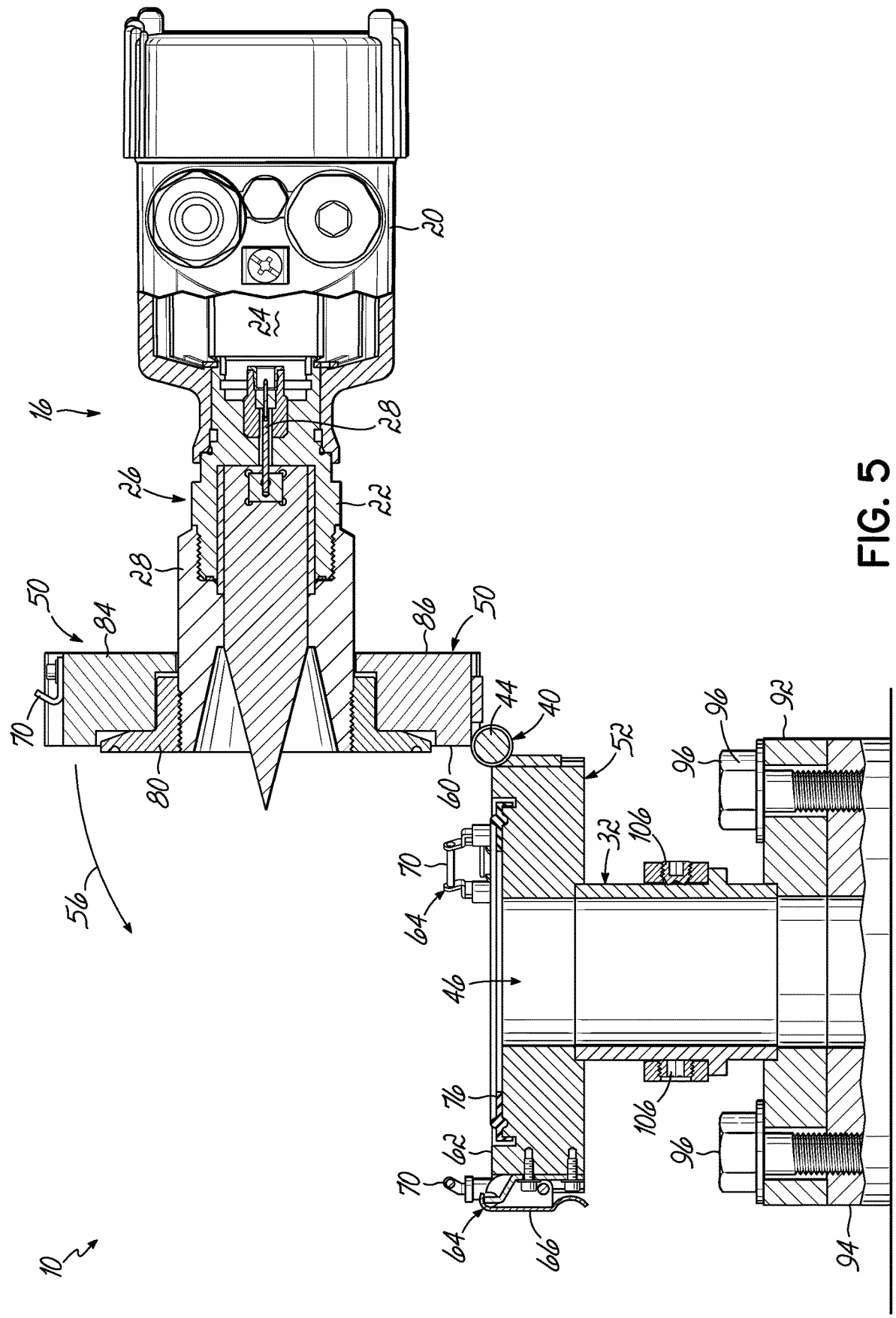
FIG. 5 is a plan view, partially in section, depicting the level sensing apparatus in an open position.

In the first exemplary embodiment, the connector assembly 40 also includes first and second flanges 50, 52 for operatively attaching housing 16 to sounding tube adaptor 32. The first, housing flange 50 is attached to and extends around the lower end of the apparatus housing 16. The second, adaptor flange 52 is attached to the upper end of sounding tube adaptor 32. The first and second flanges 50, 52 are operatively coupled together by flexible joint 44. In the illustrated embodiment, flexible joint 44 is a hinge having a first leaf secured to an outer edge of housing flange 50 and a second leaf secured to an adjacent outer edge of adaptor flange 52. Hinge 44 enables housing flange 50 to rotate relative to adaptor flange 52 along the horizontal axis 42. Rotating housing flange 50 away from the sounding tube adaptor 32, in the direction indicated by arrow 54, exposes an opening 46 to the sounding tube 12, to allow for measurement of the purity of the contents in the tank 14, and/or manual measurement of the content level using a plumb line and plumb bob. In the embodiment shown, hinge 44 is a friction hinge to hold the position of housing 16 when rotated open, as shown in FIGS. 4 and 5. Housing flange 50 can rotate from a plane substantially parallel to the open end of the sounding tube 12, to a plane substantially orthogonal to the open end of the sounding tube, with hinge 44 allowing the housing flange to be positioned at points in between the horizontal and vertical planes. Housing flange 50 and adaptor flange 52 include adjoining planar faces 60, 62 which abut in a horizontal plane when level sensing apparatus 10 is in a closed position. Additionally, the flanges 50, 52 include coaxial openings extending through each flange to provide an operative path for waves from antenna assembly 26 to pass through the connector assembly 40 and into the sounding tube 12.

For pulse radar liquid level measurement, housing flange 50 is rotated downward towards adaptor flange 52, as indicated by arrow 56, to abut the adjoining flange faces 60, 62 in the horizontal plane. Rotating the upper, housing flange 50 down into a closed position in contact with the lower, adaptor flange 52 positions the antenna assembly 26 in axial alignment with the opening through the sounding tube adaptor 32. In the closed position, waves may be transmitted from antenna assembly 26, through sounding tube adaptor 32, and sounding tube 12, to the surface of the contents of the tank. The waves are reflected from the contents surface, through the co-axial openings in sounding tube adaptor 32 and connector assembly 40, back to antenna assembly 26. The received waves are compared with the transmitted waves by a processor in apparatus 10 to calculate measurements of the tank content level. The level measurements can be output to display 30 of the housing 16.

As shown in FIGS. 2-5, connector assembly 40 includes one or more releasable locking members 64 for fixing the position of housing 16 on sounding tube adaptor 32 during pulse radar level measurements. In the illustrated embodiment, a plurality of locking members 64 is spaced about the perimeter of connector assembly 40. A first portion of each locking member 64 is attached to housing flange 50 and a second portion is attached to the adaptor flange 52, with the first portion of the locking member engaging the second portion to lock the two flanges together. In the illustrated embodiment, latches 66 are attached to adaptor flange 52, and the corresponding mating hooks 70 are attached to housing flange 50, in vertical alignment with each latch. A pin 72 on each latch is secured over the mating hook 64, and a tab on each latch pushed down, to lock the latch, and affix housing 16 to sounding tube adaptor 32. Locking housing 16 to sounding tube adaptor 32 prevents relative movement between the housing and adaptor during level measurements. The illustrated embodiment includes three locking members 64 spaced about the periphery of flanges 50, 52. However, the number and type of locking members used to affix the flanges 50, 52 together and prevent relative movement therebetween can vary from that shown, without departing from the scope of the invention. One or more sealing members, such as, for example, an o-ring 76, is provided on at least one of the planar abutting flange faces 60, 62. The o-ring 76 is compressed between the flange faces 60, 62 when the flanges are in the closed, locked position to seal the connector assembly 40.

Housing 16 further includes a lap joint 80 encircling the base of antenna shield 28. Lap joint 80 allows housing flange 50 to be attached to the housing 16, while enabling the housing to rotate relative to the flange about a vertical axis 74, shown in FIG. 4, when locking members 64 are in an unlocked position. When housing 16 is in a closed position, and locking members 64 are closed and locked, lap joint 80 is compressed against o-ring 76 in the face of adaptor flange 52. In addition to sealing connector assembly 40, the compression of the o-ring 76 against the lap joint 80 further prevents relative movement between the housing 16 and sounding tube adaptor 32 during level sensing measurements.

Figure 6:
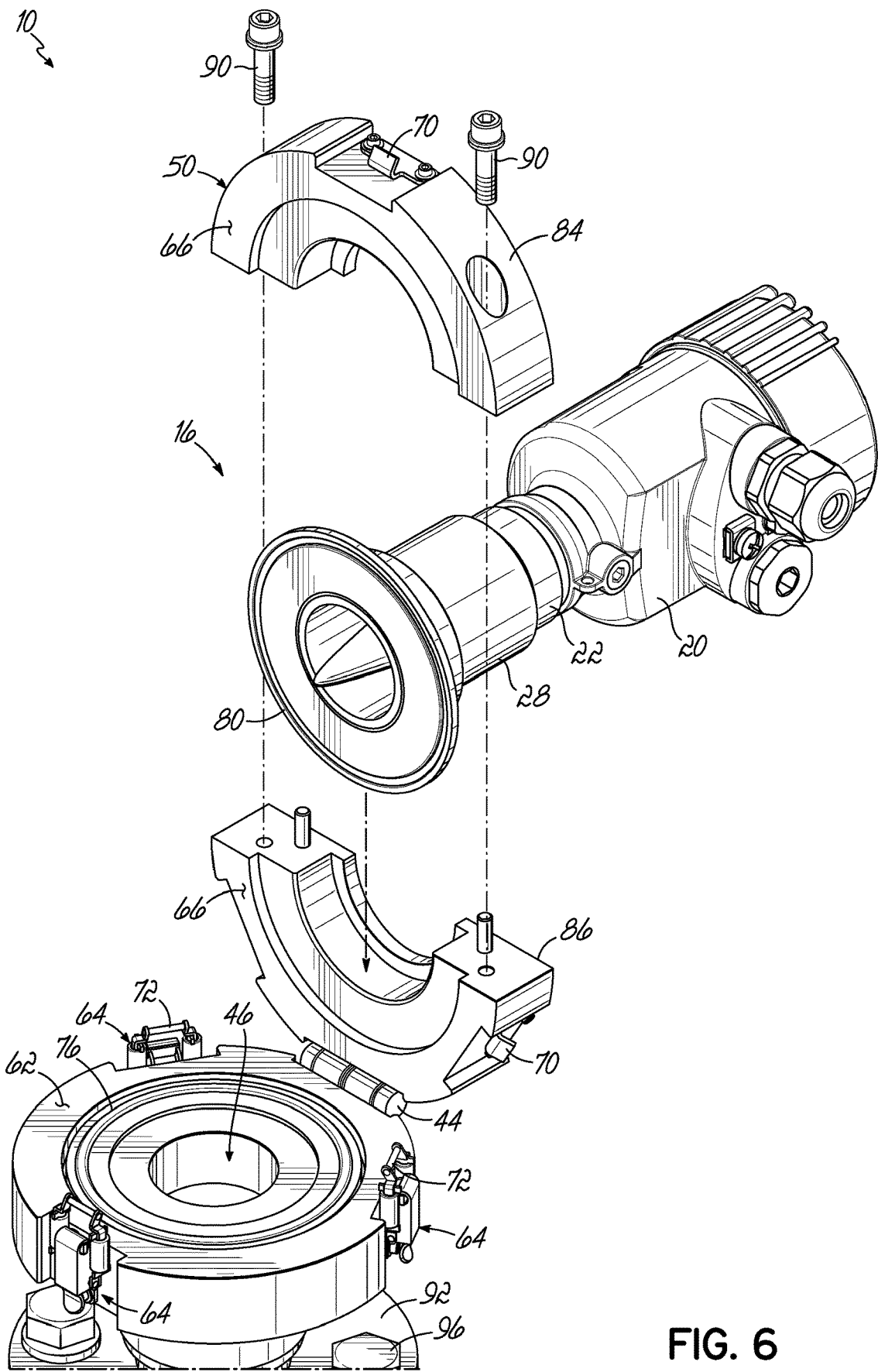
FIG. 6 is a perspective view of the level sensing apparatus depicting the first flange separated from the housing.

As shown in FIGS. 2 and 6, in the illustrated embodiment the housing flange 50 is separable into segments along a vertical plane 82. Housing flange 50 may be divided into two segments 84, 86 as shown, with one segment fixed to hinge 44. Segments 84, 86 can be held together about the base of housing 16 by releasable fasteners 90. Fasteners 90 may be removed to separate the first segment 84 from the second, hinged segment 86, when connector assembly 40 is in an unlocked condition, as shown in FIG. 6. Separating segments 84, 86 of housing flange 50 enables the radar level sensor housing 16 to be removed and replaced without the need to disassemble apparatus 10 from the sounding tube 12.

Level sensing apparatus 10 is attached to the open end of sounding tube 12 at the distal end of the sounding tube adaptor 32. The sounding tube 12, to which the level sensing apparatus 10 is attached, serves as a waveguide for directing microwave radar pulses into, and receiving microwave radar pulses from, the contents of the tank 14. The attachment of the level sensing apparatus 10 to the sounding tube 12 is facilitated by a mounting flange 92 located at and operatively connected to the end of the sounding tube adaptor 32. Mounting flange 92 is operatively coupled with a corresponding anchor plate 94, affixed to the upper platform of the storage tank 14, around the open end of the sounding tube 12. Mounting flange 92 includes a plurality of circumferentially spaced holes corresponding to holes in the anchor plate 94. Fasteners, such as screws 96, are position in the mounting flange holes and screwed down into the anchor plate 94 in order to secure apparatus 10 to the exterior of the tank. In addition to a mounting flange, the sounding tube adaptor 32 may include other, alternative attachment mechanisms for securing the level sensing apparatus 10 to the end of the sounding tube 12. These alternative attachment mechanisms can include a union fitting on the sounding tube adaptor for screwing the adaptor onto the sounding tube 12.

Connector assembly 40 provides for pulse radar and manual plumb line level measurements, as well as thief sampling to check the purity of the tank contents. In particular, to take pulse radar measurements of liquid levels in tank 14, housing 16 is rotated down into a closed position, with the housing flange 50 in an abutting relation with the adaptor flange 52. The flanges 50, 52 are locked together using locking members 64. In the closed position, the axis of symmetry of the antenna assembly 26 is in substantial axial alignment with the axis of symmetry of the sounding tube adaptor 32.

To insert a thief sampler into the sounding tube 12 to measure the purity of the tank contents, or to perform a manual level measurement, housing 16 is rotated away from the sounding tube adaptor 32 to expose the open end of the sounding tube 12. To move housing 16, locking members 64 are unlocked by pushing each of the tabbed ends outward to release pins 72 from the corresponding hooks 70 on the housing flange 50. With flanges 50, 52 unlocked, housing 16 is tilted about hinge 44 by applying a force to the housing, or the flange 50, in the direction of arrow 54. As force is applied to the housing 16, the housing rotates about the horizontal axis 42 in a direction away from the adaptor flange 52. As housing 16 rotates, the axis of symmetry of antenna assembly 26 moves out of axial alignment with the axis of symmetry of sounding tube adaptor 32, and the opening of sounding tube 12 is exposed.

Once access to the sounding tube 12 has been achieved, a thief sampler may be inserted into the interior of the sounding tube, whereby the thief sampler falls by force of gravity into the contents of the tank. The thief sampler is then retracted from the sounding tube 12, and a purity measurement of the tank contents obtained by measuring the purity of the sample collected by the thief sampler. Following collection of the sample, the housing 16 may be rotated to a downward, operative position by applying a force to housing 16 (or flange 50), to rotate the housing about hinge 44, in the direction of arrow 56, until the inner face 60 of housing flange 50 contacts the inner face 62 of adaptor flange 52. With the two flanges in a co-planar position, locking members 64 can be reengaged by positioning pins 72 over hooks 70 and pressing the latch tabs down into a locked position. With the housing flange 50 locked to the adaptor flange 52, the antenna assembly 26 is returned to axial alignment with the sounding tube adaptor 32 for pulse radar level sensing.

Figure 7:
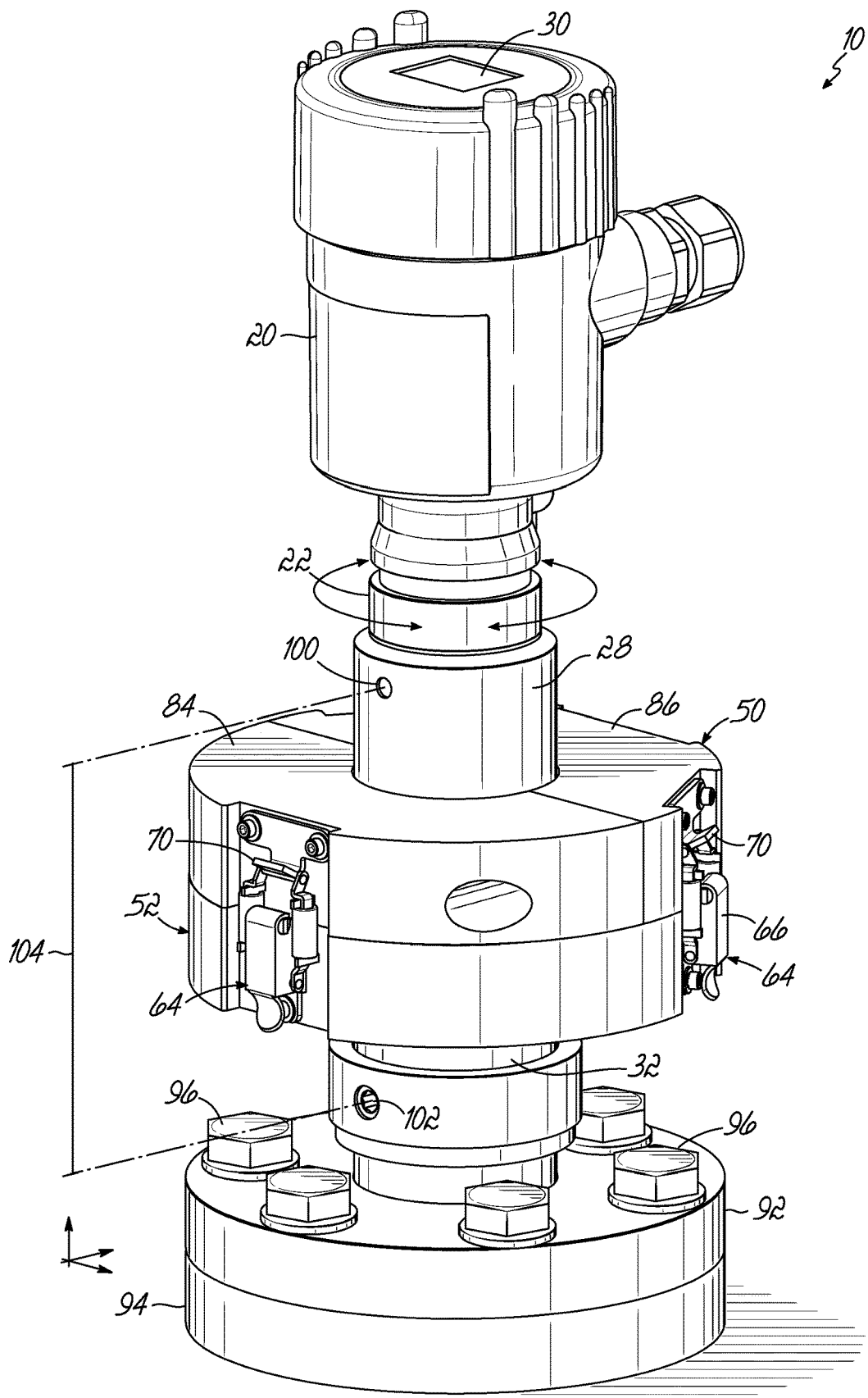
FIG. 7 is a perspective view of the level sensing apparatus, shown with the housing rotated relative to the view of FIG. 2, to show alignment indicator markings.

During rotation of housing 16 about hinge 44, the housing can move relative to flange 50. In particular, the housing 16 can rotate about the axis 74 shown in FIG. 4. The movement of housing 16 relative to the sounding tube adaptor 32 can disrupt the alignment between the antenna assembly 26 and the sounding tube 12, which serves as a waveguide for propagation of the radar wave pulses from the antenna assembly to the surface of the tank contents. To obtain precise level measurements, it is important to maintain optimum polarization between the level sensing apparatus 10 and the sounding tube 12. To facilitate optimum polarization, level sensing apparatus 10 includes polarization "sweet spot" indicator markings. As shown in FIG. 7, these markings, indicated at 100 and 102, are provided on an exterior surface of both the housing 16 and the sounding tube adaptor 32. When indicator markings 100, 102 are vertically aligned, as indicated by line 104 in FIG. 7, the antenna assembly 26 in apparatus 10 is optimally polarized with the sounding tube 12.

It is anticipated that the position of indicator marking 102 on the circumference of sounding tube adaptor 32 will be fixed as part of the instrument calibration at the time of installation of the adaptor onto the sounding tube 12. The indicator marking 102 can be fixed in position relative to the sounding tube 12, to prevent rotation relative to the tube, by any type of securing device, such as a set screw 106 shown in FIG. 5. Fixing the position of the indicator marking 102 on sounding tube adaptor 32 enables the marking to serve as an alignment set point. After housing 16 has been opened for a manual level measurement or purity check, the polarization of the antenna assembly 26 and sounding tube 12 can be verified by checking the vertical alignment of indicator markings 100, 102. If the marking 100 on housing 16 is out of vertical alignment with the adaptor indicator marking 102, the housing flange 50 can be unlocked from the adaptor flange 52, and the housing rotated within the housing flange, relative to the sounding tube adaptor 32. The housing 16 is rotated until the two indicator markings 100, 102 are in vertical alignment. When the indicator markings 100, 102 are vertically aligned, connector assembly 40 can be locked to prevent further movement of the housing 16.

Figure 8:
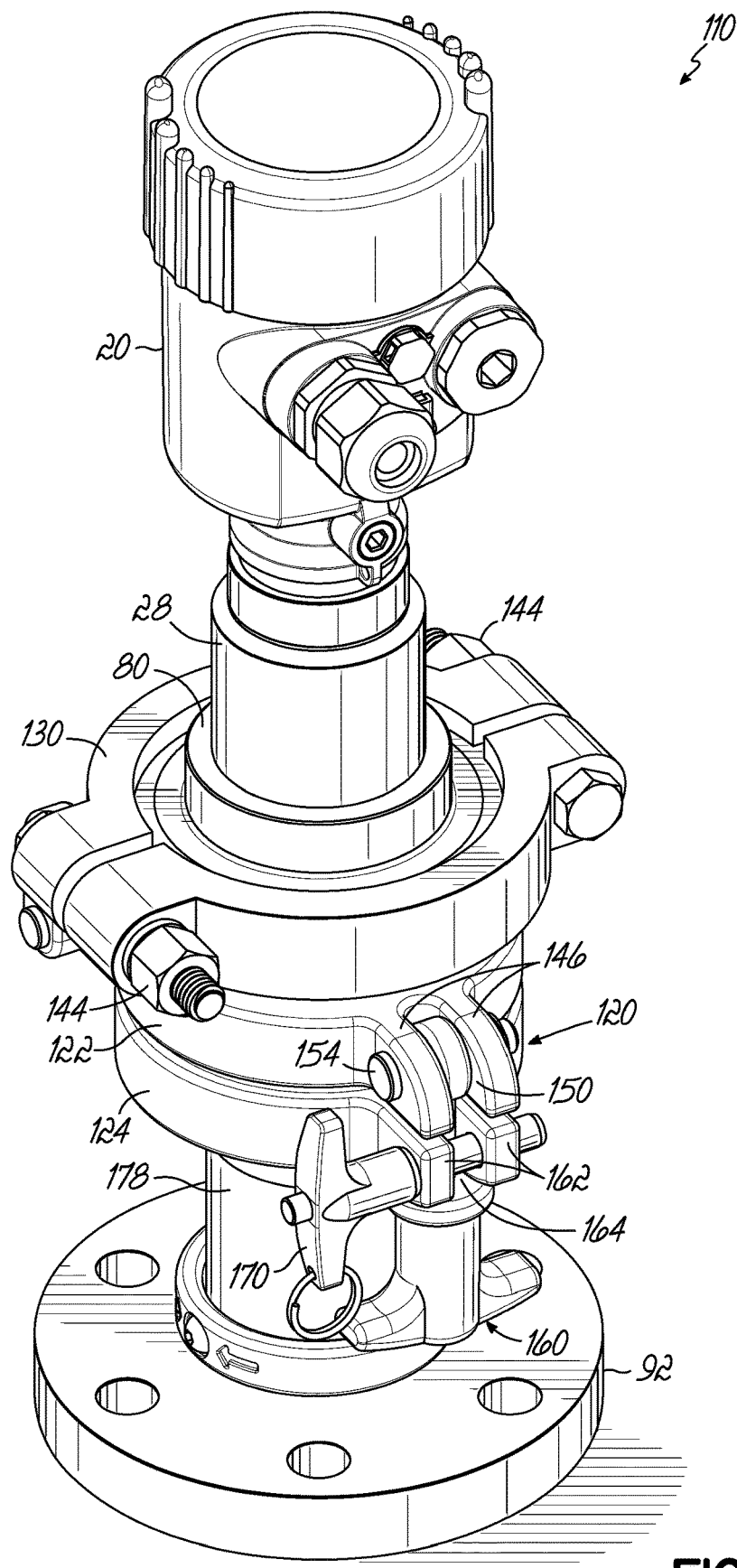
FIG. 8 is a perspective view of an alternative embodiment of a level sensing apparatus depicting the apparatus in a closed, locked position.
Figure 9:
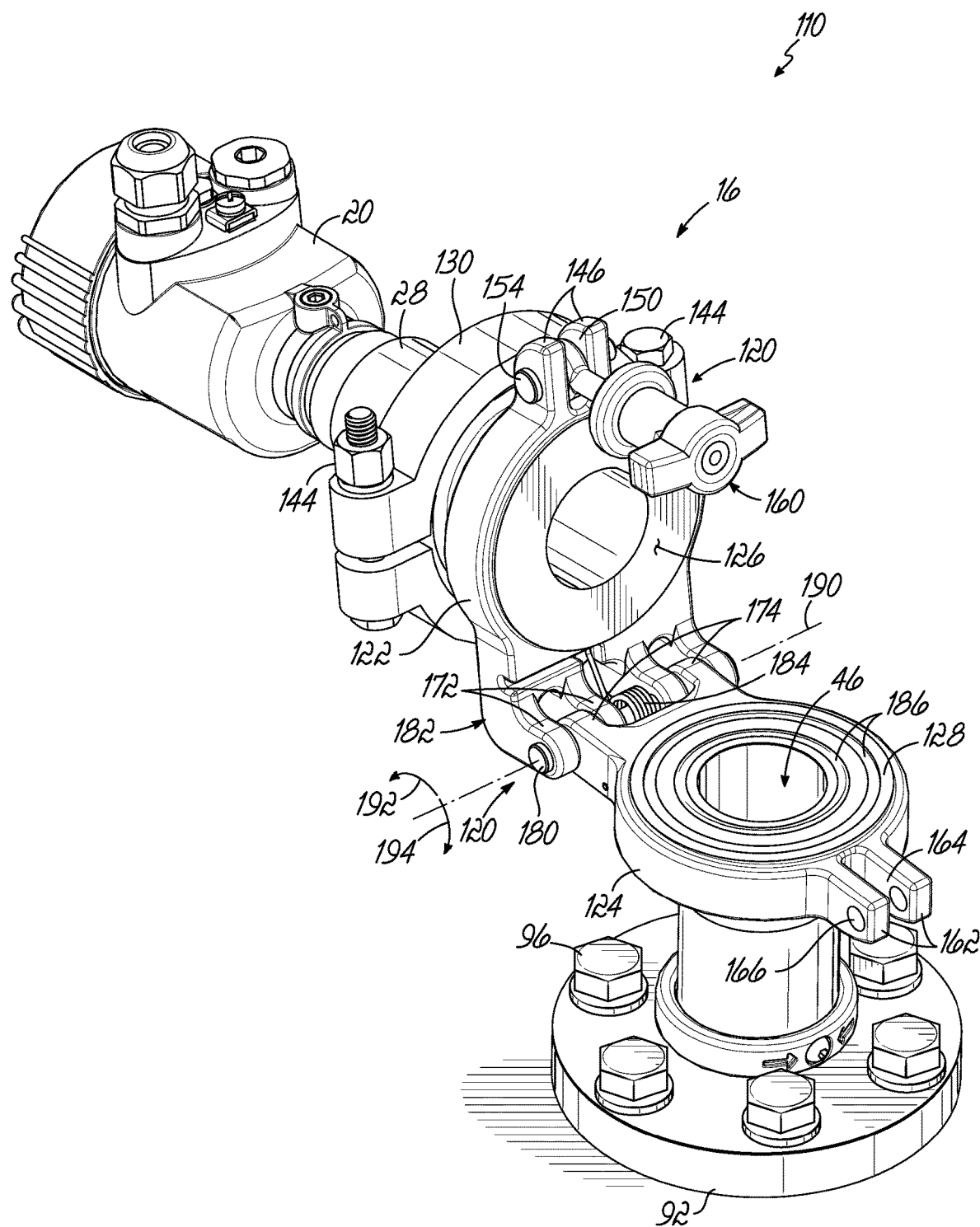
FIG. 9 is a perspective view of the alternative embodiment of FIG. 8, depicting the level sensing apparatus in an open position.

FIGS. 8 and 9 depict a second exemplary embodiment for a level sensing apparatus. In this embodiment, the level sensing apparatus 110 includes an alternative connector assembly 120 for operatively connecting the level sensing housing 16 to the sounding tube 12. The connector assembly 120 includes a first, upper flange 122 and a second, lower flange 124 for rotating the level sensing housing 16 relative to the sounding tube 12. The upper and lower flanges 122, 124 have planar surfaces 126, 128 which abut when the connector assembly 120 is in a closed position. Additionally, flanges 122, 124 include coaxial openings extending through each flange to provide an operative path for waves to pass through the connector assembly 120 between the antenna assembly 26 and the sounding tube 12. In this embodiment, a portion of lower flange 124 is shaped to provide a cylindrical, sounding tube extension, as indicated at 178, for attaching the connector assembly 120 to the sounding tube 12. Sounding tube extension 178 replaces the sounding tube adaptor 32 used in the previous embodiment for attaching the connector assembly to the sounding tube.

Figure 10:
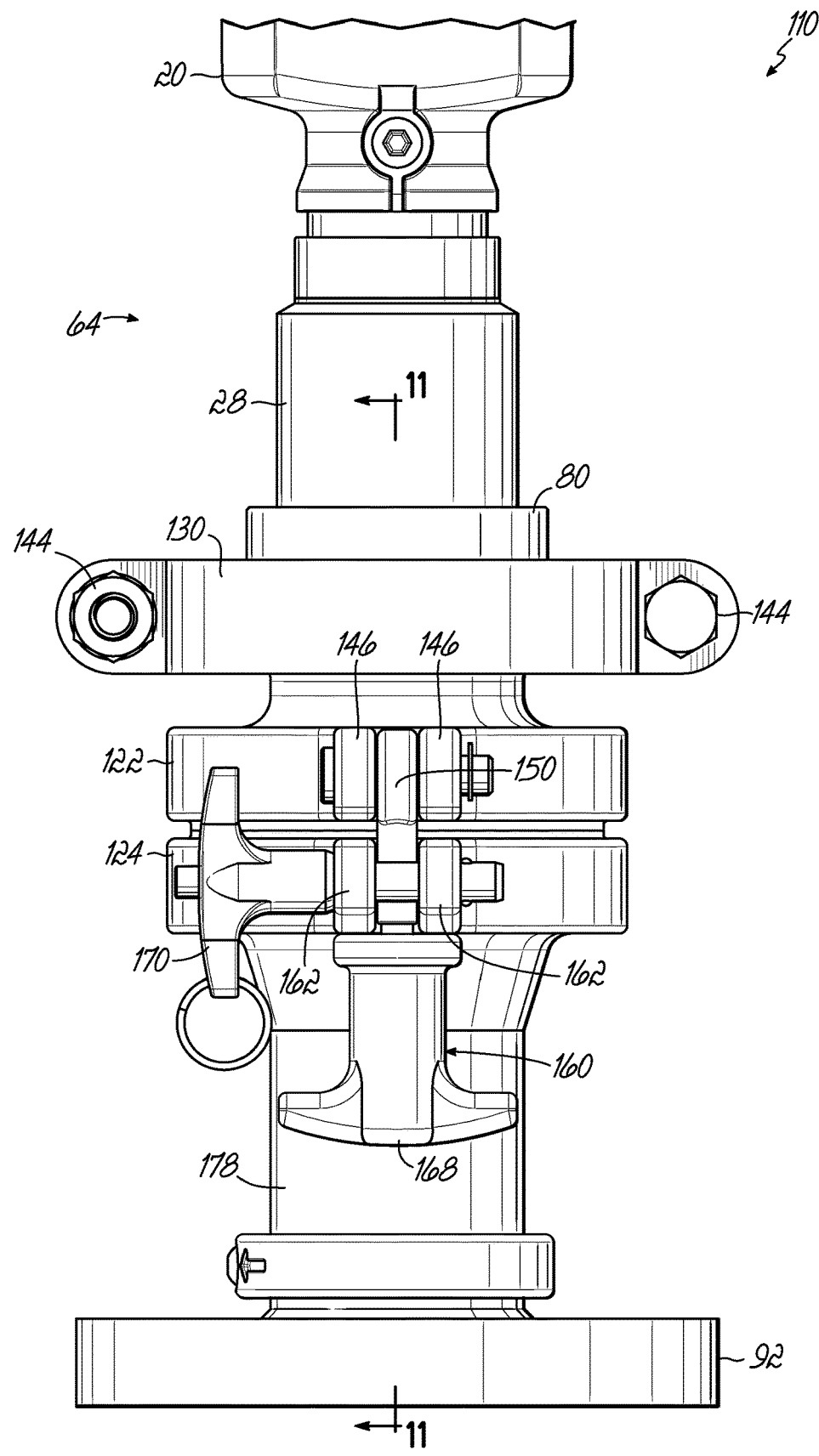
FIG. 10 is a side plan view of the level sensing apparatus of FIG. 8.
Figure 11:
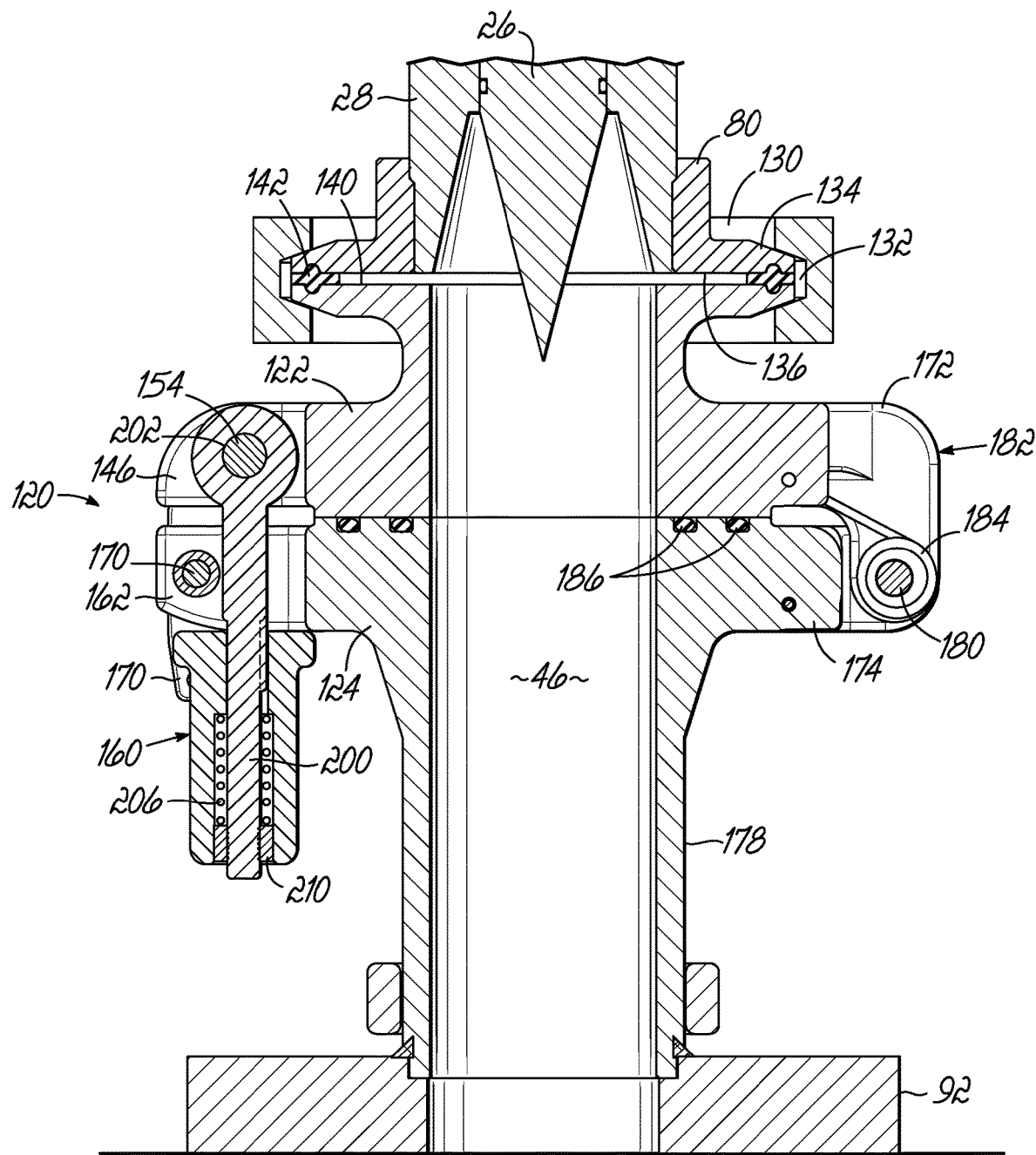
FIG. 11 is a cross-sectional view of the connector assembly for the alternative embodiment of FIG. 8, taken along line 11-11 of FIG. 10.

A clamp 130, having a pair of releasably-connected, semi-circular segments, encircles the apparatus 110 for connecting the housing 16 to the first flange 122 of the connector assembly 120. Referring to FIGS. 10 and 11, clamp 130 has a recessed interior area 132 extending about the circumference of the clamp. As described in the first embodiment, a lap joint 80 encircles the base of the antenna shield 28. Clamp 130 engages a flange 134 on the lap joint 80 within the interior area 132. Lap joint 80 has a planar bottom surface 136 which abuts a planar top surface 140 of the upper flange 122. One or more sealing members, such as, for example, an o-ring 142, are positioned between the planar surfaces 136, 140 to seal the opening between the surfaces. Clamp 130 engages the outer circumference of the lap joint 80 and upper flange 122 to lock the edges together. Clamp 130 is formed in two semi-circular halves connected by releasable fasteners 144. When connected, clamp 130 locks apparatus housing 16 to the connector assembly 120. Fasteners 144 are removable to separate clamp 130, and allow for the removal and replacement of the housing 16.

As shown in FIGS. 8-10, upper flange 122 includes a pair of radially-outward extending arms 146, with a slot, indicated at 150, therebetween. Arms 146 include horizontally-aligned through holes for retaining a pivot pin 154. A handle 160 is mounted on pin 154 to pivot vertically thereon between an upper, open position and a lower, closed position. Lower flange 124 includes a pair of arms 162 spaced apart to form a slot, indicated at 164. Slot 164 has a similar size as, and is vertically aligned with, the upper flange slot 150. Handle 160 slides into the lower flange slot 164 when the handle is pivoted into a downward, closed position. When engaged in lower flange slot 164, handle 160 functions as a locking member for affixing the housing to the sounding tube. Lower flange arms 162 may include axially aligned through holes 166. A removable pin 170 may be inserted into holes 166 when handle 160 is in a downward position inside slot 164, in order to prevent the handle from disengaging from the slot. Pin 170 may be further configured with a locking mechanism (not shown) to prevent unauthorized removal of the pin from the lower flange arms 162.

Figure 12A:
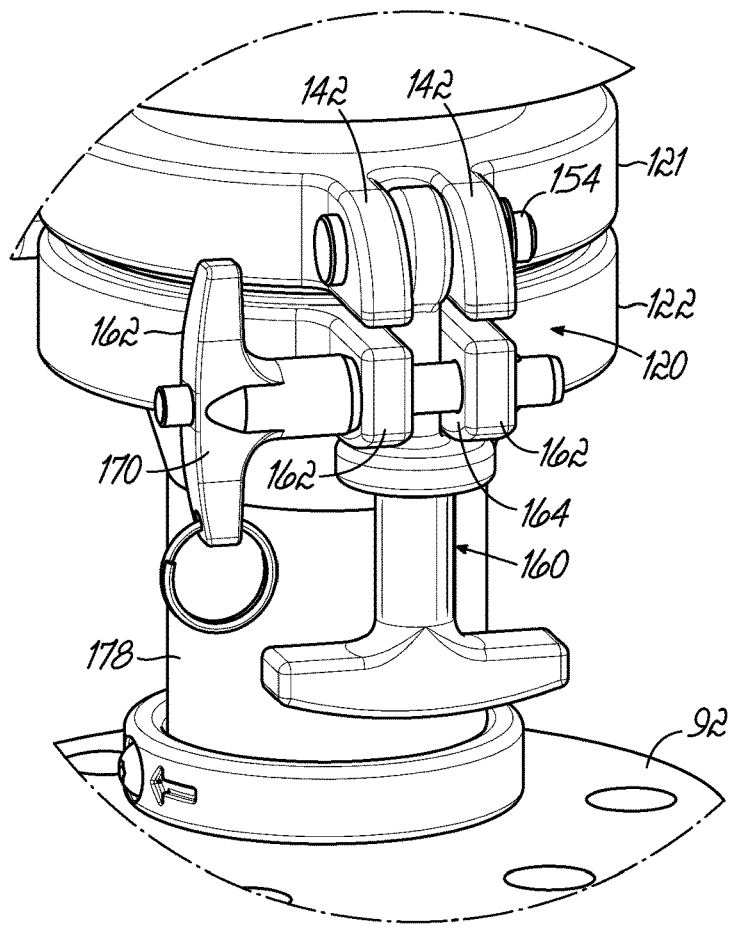
FIG. 12A is a first embodiment of a handle shown in a locking position.
Figure 12B:
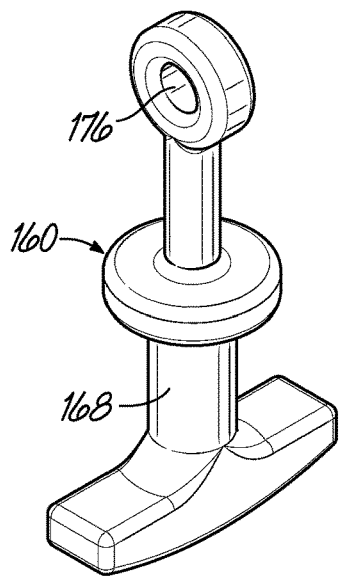
FIG. 12B is an isolated, perspective view of the handle depicted in FIG. 12A.
Figure 13A:
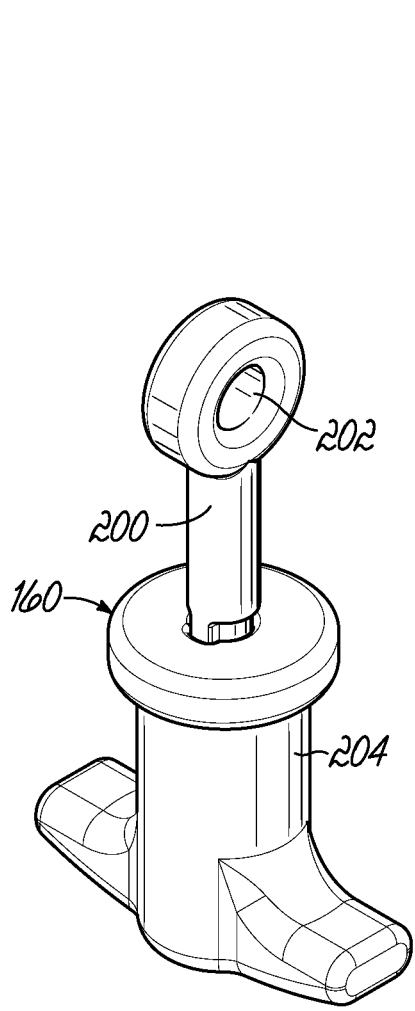
FIG. 13A is a perspective view of a second embodiment of a handle.
Figure 13B:
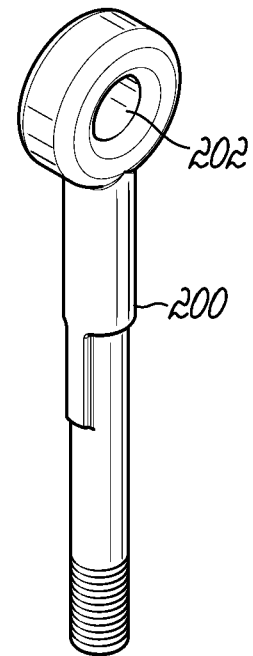
FIG. 13B is an exploded view of the handle depicted in FIG. 13A.
Figure 13B:
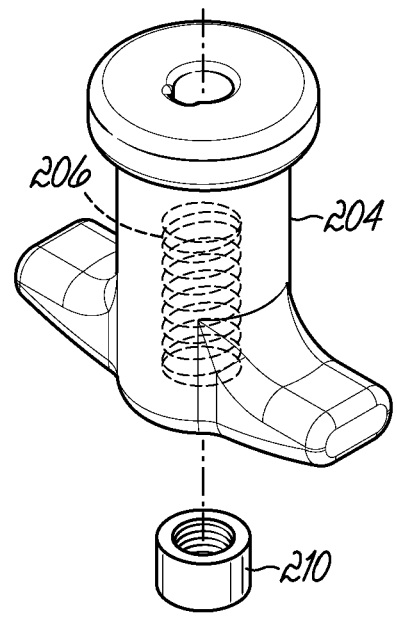

FIGS. 12A and 12B illustrate a first embodiment for the handle 160. In this embodiment, the handle 160 has a unitary structure with a through hole 176 for engaging pin 154 at one end, and a pull 168 at the other end. FIGS. 13A and 13B illustrate a second embodiment for handle 160. In this embodiment, the handle comprises a link member 200 having a through hole 202 for engaging pin 154 at one end. A pull member 204 is moveably mounted on the opposite end of the link member 200. A spring 206 encircles the link member 200 within a recess formed in the pull member 204. Spring 206 is retained between a nut 210 screwed onto the base of link member 200, and the pull member 204, to bias the pull member 204 in the direction of lower flange 124. In this embodiment, the force of spring 206 drives the pull member 204 upward against lower flange arms 162. The upward force of pull member 204 drives the lower flange 124 into closer contact with the upper flange 122. The upward force on pull member 204 can be adjusted by adjusting the position of nut 210 on link member 200 to alter the tension of the spring.

Figure 14A:
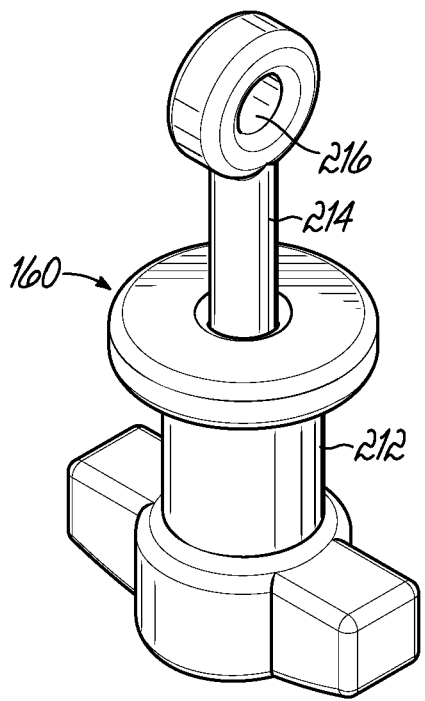
FIG. 14A is a perspective view of a third embodiment of a handle.
Figure 14B:
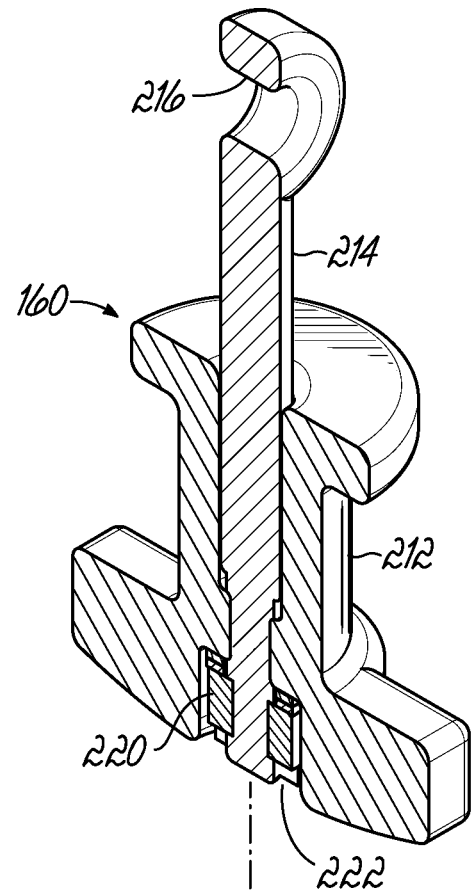
FIG. 14B is a cross-sectional view of the handle depicted in FIG. 14A, shown with a fitting for adjusting the handle.
Figure 14B:
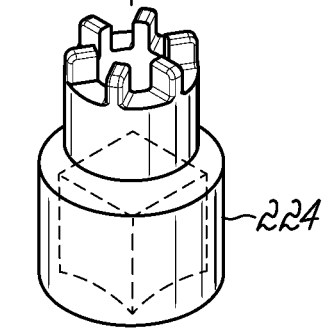

FIGS. 14A and 14B illustrate a third embodiment for handle 160. In this embodiment, the handle includes a pull member 212, and a link member 214 having a through hole 216 at one end for engaging pin 154. At least one locking washer 220 is attached to the opposite end of the link member 214, such as by screw threads, in a recessed area 222 at the base of pull member 212. The position of washer 220 on link member 214 may be adjusted relative to the pin 154 to alter the distance between the pull member 212 and the pin. Washer 220 can have apertures designed for receiving a specialized fitting 224. Fitting 224 can be attached to a torque wrench to provide the correct adjustment of the washer. Using a specialized fitting 224 allows for increased control over the washer adjustment. The fitting 224 depicted in FIG. 14B is merely representative of the type of fitting that may be used to adjust washer 220. Other types of fittings, having a variety of configurations, may be used in order to ensure only authorized, secure adjustments of the washer 220. Adjusting washer 220 to decrease the distance between the pull member 212 and pin 154 increases the pressure between the pull member and the bottom of lower flange arms 162 when the handle is downwardly engaged in the lower flange slot 164. This increased pressure causes the lower flange 124 to be pushed closer towards the upper flange 122.

Returning now to FIG. 9, opposite handle 160, upper flange 122 extends outward to form a plurality of downwardly extending knuckles 172. Similarly, lower flange 124 includes a plurality of radially-outward extending knuckles 174. Knuckles 174 on the lower flange 122 interleave with knuckles 172 on the upper flange 124. A pin 180 extends through holes in the upper and lower knuckles 172, 174 to form a flexible joint or hinge 182 for rotating the upper flange 122 relative to the lower flange 124 between open and closed positions. Hinge 182 joins the edges of the upper and lower flanges 122,124 along a horizontal axis 190 passing longitudinally through the hinge pin 180. A torsion spring 184 is mounted on pin 180 to facilitate rotation of the upper flange 122 away from the lower flange 124.

As mentioned above, upper and lower flanges 122, 124 include planar surfaces 126, 128 which abut each other in the closed position. One or more sealing members, such as, for example, an o-ring 186, are provided in one or both planar surfaces 126, 128. The o-rings 186 are compressed between the abutting flange surfaces 126, 128 when the flanges are in a closed position to seal the connector assembly 120 and prevent the release of gases and/or odors from the sounding tube 12.

Similar to the first embodiment described above, the connector assembly 120 of the second level sensing apparatus embodiment 110 provides for pulse radar and manual plumb line level measurements, as well as thief sampling to check the purity of the tank contents. In particular, to take pulse radar measurements of liquid levels in tank 14, housing 16 is rotated down into a closed position, with the upper flange 122 abutting the lower flange 124. In this embodiment, the flanges 122, 124 are maintained in a closed position by sliding handle 160 down between lower flange arms 162. In the closed position, the axis of symmetry of the antenna assembly 26 is in substantial axial alignment with the axis of symmetry of the sounding tube 12 to allow for radar level sensing measurements.

To insert a thief sampler into the sounding tube 12 to measure the purity of the tank contents, or to perform a manual level measurement, housing 16 is rotated away from the lower flange 124 to expose an opening 46 into the sounding tube 12. To move housing 16, retaining pin 170 is pulled out from holes 166 in lower flange arms 162. With pin 170 removed, handle 160 can be pivoted out from slot 164 between lower flange arms 162. With handle 160 free of the lower flange 124, torsion spring 184 rotates the upper flange 122 and attached housing 16 away from the lower flange 124 about a horizontal axis 190, as indicated by arrow 192 in FIG. 9. As the connector assembly 120 pivots on hinge 182, the connector assembly rotates a lower end of the housing 16 relative to the sounding tube 12 about the horizontal axis 190 from a plane substantially parallel to the open end of the sounding tube to a plane having at least a 90 degree angle relative to the open end of the sounding tube. Rotating housing 16 draws the axis of symmetry of antenna assembly 26 out of axial alignment with the axis of symmetry of the sounding tube 12 and exposes the opening 46 of the sounding tube.

Once access to the sounding tube 12 has been achieved, a thief sampler may be inserted into the interior of the sounding tube, whereby the thief sampler falls by force of gravity into the contents of the tank. The thief sampler is then retracted from the sounding tube 12, and a purity measurement of the tank contents obtained by measuring the purity of the sample collected by the thief sampler. Following collection of the sample, the connector assembly 120 may be returned to a closed, operative position by applying a pulling force to handle 160 to rotate the upper flange 122, clamp 130 and attached housing 16 about hinge 182, in the direction of arrow 194, until the planar inner surface 126 of upper flange 122 makes operative contact with the inner surface 128 of lower flange 124. With the planar surfaces of the upper and lower flanges 122, 124 abutting in a closed position, handle 160 can be slid down into lower flange slot 164. Retaining pin 170 can be inserted through holes 166 in the lower flange arms 162 to lock the handle 160, as well as the connector assembly 120, in a downward, closed position. With the upper flange 122 locked to the lower flange 124, the antenna assembly 26 is returned to axial alignment with the sounding tube 12.

Figure 15:
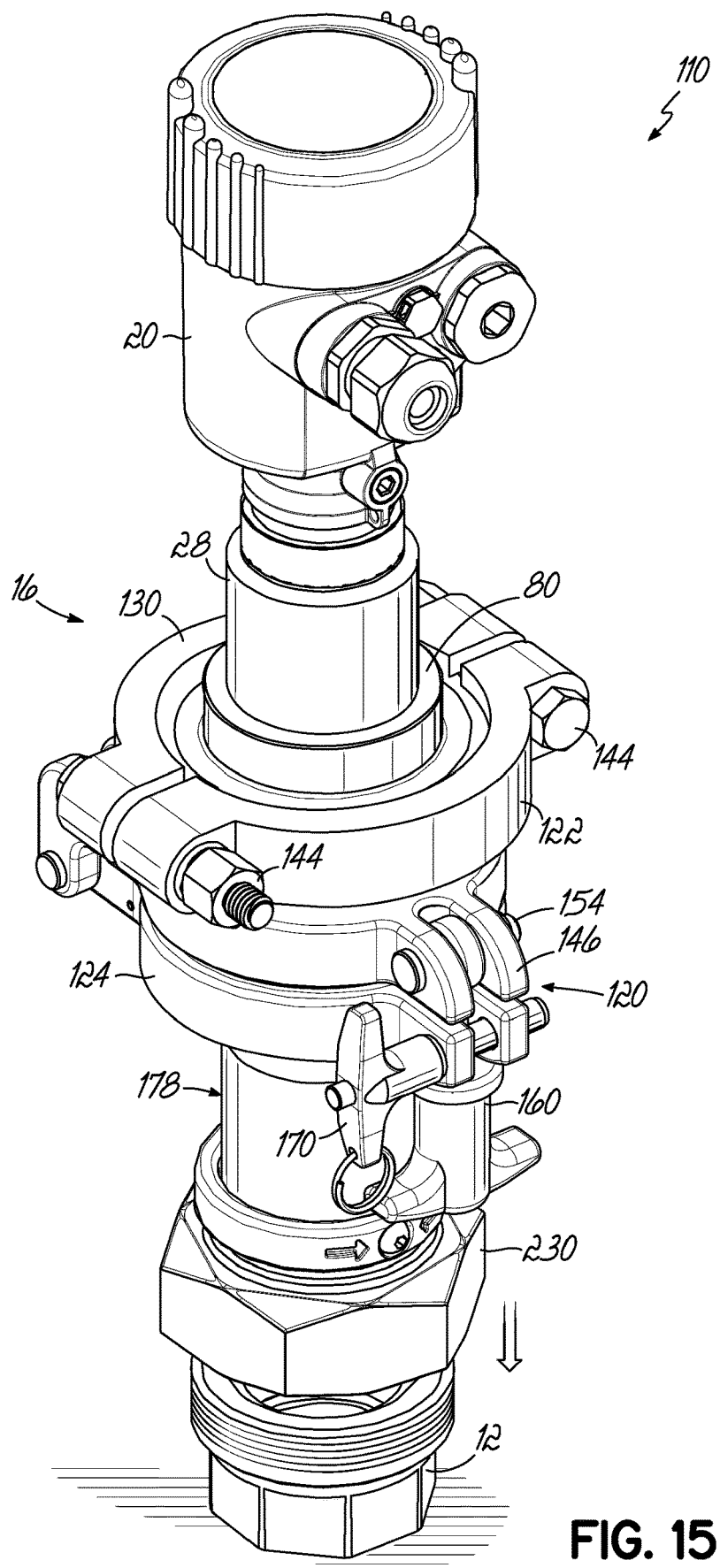
FIG. 15 is a perspective view of the level sensing apparatus of FIG. 8, shown with an alternative embodiment for mounting the apparatus on a sounding tube.

Similar to the first embodiment described above, the level sensing apparatus 110 may be attached to the sounding tube 12 by a mounting flange 92 operatively connected to the sounding tube extension 178. The mounting flange 92 may be operatively coupled with a corresponding anchor plate 94, affixed to the upper platform of the storage tank 14, around the open end of the sounding tube 12. In addition to a mounting flange, the connector assembly 120 may include other, alternative attachment mechanisms for securing the level sensing apparatus 110 to the end of the sounding tube 12. As shown in FIG. 15, these alternative attachment mechanisms can include a union fitting 230 attached to the lower end of sounding tube extension 178 for screwing the connector assembly 120 onto the top of sounding tube 12.

The present invention has been described in connection with several embodiments and some of those embodiments have been elaborated in substantial detail. However, the scope of the invention is not to be limited by these embodiments which are presented as exemplary and not exclusive. The scope of the invention being claimed is set forth by the following claims.

What is claimed is:

1. A level sensing apparatus for attachment to a sounding tube to measure content levels in a tank, the level sensing apparatus comprising:
   a housing;
   a transmitter disposed within the housing;
   an antenna disposed within the housing and operatively connected to the transmitter for directing electrical or mechanical waves in a direction away from the transmitter, the antenna further adapted to receive electrical and mechanical waves; and
   a connector assembly operatively attaching the housing to the sounding tube, the connector assembly adapted to allow the housing to rotate relative to the connector assembly about a vertical axis extending through the sounding tube, and further allow the housing to rotate relative to the sounding tube about a horizontal axis to expose an open end of the sounding tube.

2. The level sensing apparatus of claim 1, wherein a lower end of the housing rotates relative to the sounding tube about the horizontal axis from a plane substantially parallel to the open end of the sounding tube to a plane having at least a 90 degree angle relative to the open end of the sounding tube.

3. The level sensing apparatus of claim 1, wherein an axis of symmetry of the housing is substantially aligned with an axis of symmetry of the sounding tube when the housing is in a closed position.

4. The level sensing apparatus of claim 1, wherein the housing is rotatable relative to the sounding tube when the first flange and the second flange are in an unlocked condition.

5. The level sensing apparatus of claim 1, wherein the connector assembly further comprises first and second flanges for operatively connecting the housing and the sounding tube.

6. The level sensing apparatus of claim 5, wherein the flanges include an opening for passage of the electrical and mechanical waves between the antenna and the sounding tube.

7. The level sensing apparatus of claim 5, further comprising a first alignment indicator on the second flange and a second alignment indicator on the housing, the housing being sufficiently rotatable relative to the sounding tube to align the first and second alignment indicators.

8. The level sensing apparatus of claim 5, wherein the connector assembly further comprises a flexible joint joining edges of the first and second flanges along the horizontal axis.

9. The level sensing apparatus of claim 8, wherein the first flange is releasably attached to the housing.

10. The level sensing apparatus of claim 8, wherein the connector assembly further comprises one or more locking members for preventing relative movement between the first and second flanges in a closed position.

11. The level sensing apparatus of claim 8, wherein the first flange is rotatable about the flexible joint between a closed position wherein the first and second flanges extend in a substantially horizontal plane, and an open position wherein the first flange extends in a plane at least 90 degrees relative to the second flange.

12. The level sensing apparatus of claim 11, wherein at least one of the first and second flanges further comprises one or more sealing members for sealing the housing to the sounding tube in a closed position.

13. A method of measuring a level of and determining a purity of contents in a tank using a sounding tube extending into the tank contents, the method comprising the steps of:
providing a level sensing apparatus attached to an open end of the sounding tube, the level sensing apparatus having a housing, a transmitter disposed within and attached to the housing, an antenna disposed within the housing and operatively connected to the transmitter for directing electrical or mechanical waves in a direction away from the transmitter and receiving electrical or mechanical waves, and a connector assembly for operatively attaching the housing to the sounding tube, the connector assembly adapted to allow the housing to rotate relative to the sounding tube about a horizontal axis;
directing the electrical or mechanical waves to a content surface in the sounding tube using the level sensing apparatus;
receiving the electrical or mechanical waves reflected from the content surface in the sounding tube using the level sensing apparatus;
obtaining a corresponding measurement of a level of the content surface in the sounding tube from the level sensing apparatus;
rotating the housing relative to the sounding tube about a vertical axis extending through the sounding tube to align polarization of the antenna to the sounding tube;
rotating the housing relative to the sounding tube about a horizontal axis to expose an open end of the sounding tube;
collecting a sample of contents in the tank; and
determining the purity of the sample.

14. The method of claim 13, wherein prior to rotating the housing, the method further comprises the steps of: providing the connector assembly with at least one locking member, the locking member being engaged to affix the housing to the sounding tube; and disengaging the locking member to move the housing away from the sounding tube.

15. The method of claim 13, further comprising the steps of: rotating the housing to substantially align the housing with the open end of the sounding tube in a horizontal plane, moving the at least one locking member to a closed position to lock the housing to the sounding tube, and obtaining an additional level measurement of the contents of the tank using the level sensing apparatus.

16. The method of claim 13, wherein after the step of rotating the housing relative to the sounding tube, the method further comprises the steps of: inserting a plumb bob and attached plumb line into the sounding tube, allowing the plumb bob to reach a bottom of the sounding tube, retracting the plumb bob from the sounding tube, reading a fuel level from the plumb line, rotating the housing over the top of the sounding tube, and aligning an indicator marking on the housing with an indicator marking on the sounding tube.

17. A level sensing apparatus for attachment to a sounding tube to measure levels of contents in a tank, the level sensing apparatus comprising:
a housing;
a transmitter disposed within the housing;
an antenna disposed within the housing and operatively connected to the transmitter for directing electrical or mechanical waves in a direction away from the transmitter, the antenna further adapted to receive electrical and mechanical waves;
a first flange connected to the housing;
a second flange having a first end adapted for attachment to a sounding tube, and a second end adapted for engaging the first flange, the first flange operatively engaging the second flange to enable the housing to rotate relative to the second flange about a vertical axis extending through the second flange and the sounding tube attached thereto, and further allow the housing to rotate away from the second flange along a horizontal axis.

18. The level sensing apparatus of claim 17, further comprising a first alignment indicator on a sounding tube adaptor and a second alignment indicator on the housing, the housing being sufficiently rotatable relative to the sounding tube adaptor to align the first and second alignment indicators.

19. The level sensing apparatus of claim 17, further comprising a clamp engaging the housing and first flange, the clamp having first and second separable segments for disconnecting the housing from the first flange.

20. The level sensing apparatus of claim 19, wherein the first and second segments of the housing flange are adapted to allow for removal of the housing from the first flange when the first and second segments are separated.

* * * * *